United States Patent
Tsuchiyama et al.

(10) Patent No.: US 9,423,390 B2
(45) Date of Patent: Aug. 23, 2016

(54) CETANE NUMBER ESTIMATION DEVICE

(75) Inventors: Makio Tsuchiyama, Toyota (JP);
Yoshiyasu Ito, Toyota (JP); Takeshi Miyaura, Toyota (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 235 days.

(21) Appl. No.: 14/004,221

(22) PCT Filed: Mar. 29, 2011

(86) PCT No.: PCT/JP2011/057806
§ 371 (c)(1),
(2), (4) Date: Sep. 10, 2013

(87) PCT Pub. No.: WO2012/131900
PCT Pub. Date: Oct. 4, 2012

(65) Prior Publication Data
US 2014/0013832 A1    Jan. 16, 2014

(51) Int. Cl.
*G01N 33/22* (2006.01)
*F02D 1/16* (2006.01)
*F02D 19/06* (2006.01)
*F02D 41/00* (2006.01)
*F02D 41/14* (2006.01)

(52) U.S. Cl.
CPC ..... *G01N 33/22* (2013.01); *F02D 1/16* (2013.01); *F02D 1/162* (2013.01); *F02D 19/061* (2013.01); *F02D 19/0636* (2013.01); *F02D 19/0649* (2013.01); *F02D 41/0025* (2013.01); *F02D 41/1497* (2013.01); *F02D 2200/0602* (2013.01); *F02D 2200/0612* (2013.01); *F02D 2200/1012* (2013.01); *Y02T 10/36* (2013.01)

(58) Field of Classification Search
CPC ........... F02D 2200/0612; F02D 19/0636; F02D 19/061; F02D 19/0649; F02D 41/0025; F02D 41/1497; F02D 2200/1012
USPC ............................................. 701/104, 105
See application file for complete search history.

(56) References Cited

U.S. PATENT DOCUMENTS

| 5,457,985 A | * | 10/1995 | Cellier et al. | 73/35.02 |
| 5,469,831 A | * | 11/1995 | Takahashi | 123/680 |
| 6,941,929 B2 | * | 9/2005 | Shinzawa | 123/357 |
| 7,027,906 B2 | * | 4/2006 | Araki | 701/104 |
| 7,195,002 B2 | * | 3/2007 | Tsutsui | 123/467 |
| 7,287,515 B2 | * | 10/2007 | Okamura et al. | 123/494 |

(Continued)

FOREIGN PATENT DOCUMENTS

| JP | 2008-082227 A | 4/2008 |
| JP | 2008-280896 A | 11/2008 |

(Continued)

*Primary Examiner* — Lisa Caputo
*Assistant Examiner* — Tran M Tran
(74) *Attorney, Agent, or Firm* — Sughrue Mion, PLLC

(57) ABSTRACT

In order to estimate the cetane number of a fuel, fuel injection is executed by controlling the driving of a fuel injection valve by a prescribed amount. The amount of change in the rotation of a diesel engine generated in response to the fuel injection is detected, and the cetane number of the fuel is estimated on the basis of this amount of change in the rotation. The actual amount of fuel injected from the fuel injection valve is detected, and when the difference between the amount actually detected and the prescribed amount is equal to or greater than a threshold value, the execution of the fuel cetane number estimation process is restricted.

4 Claims, 8 Drawing Sheets

(56) References Cited

U.S. PATENT DOCUMENTS

| | | | |
|---|---|---|---|
| 7,289,900 B2* | 10/2007 | Wilharm et al. | 701/103 |
| 7,296,556 B2* | 11/2007 | Yamaguchi | F02D 35/023 |
| | | | 123/305 |
| 7,322,341 B2* | 1/2008 | Yamaguchi | F02D 35/023 |
| | | | 123/27 R |
| 7,367,223 B2* | 5/2008 | Kettl et al. | 73/53.05 |
| 7,401,591 B2* | 7/2008 | Yamaguchi | F02D 35/023 |
| | | | 123/299 |
| 7,421,884 B2* | 9/2008 | Aoyama | 73/35.02 |
| 7,444,984 B2* | 11/2008 | Yamaguchi et al. | 123/406.47 |
| 7,480,557 B2* | 1/2009 | Yamaguchi | F02D 35/023 |
| | | | 123/299 |
| 7,621,174 B2* | 11/2009 | Takaku | 73/114.53 |
| 7,673,618 B2* | 3/2010 | Hasegawa et al. | 123/435 |
| 7,926,331 B2* | 4/2011 | Tsutsumi et al. | 73/114.38 |
| 7,987,696 B2* | 8/2011 | Kuronita et al. | 73/35.02 |
| 8,027,781 B2* | 9/2011 | Tanaka | F02D 19/0684 |
| | | | 123/436 |
| 8,042,517 B2* | 10/2011 | Nakajima | 123/406.41 |
| 8,051,836 B2* | 11/2011 | Moriya | 123/435 |
| 8,060,292 B2* | 11/2011 | Takahashi et al. | 701/104 |
| 8,073,638 B2* | 12/2011 | Birk et al. | 702/30 |
| 8,074,503 B2* | 12/2011 | Tsutsumi et al. | 73/114.38 |
| 8,150,596 B2* | 4/2012 | Kweon et al. | 701/103 |
| 8,191,412 B2* | 6/2012 | Doring | 73/114.71 |
| 8,224,554 B2* | 7/2012 | Kondo et al. | 701/104 |
| 8,266,947 B2* | 9/2012 | Yoeda | 73/35.02 |
| 8,281,643 B2* | 10/2012 | Yasuda | 73/35.02 |
| 8,307,695 B2* | 11/2012 | Miyaura et al. | 73/35.02 |
| 8,423,267 B2* | 4/2013 | Iwatani | 701/105 |
| 8,532,911 B2* | 9/2013 | Haskara et al. | 701/105 |
| 8,538,664 B2* | 9/2013 | Miyaura | F02D 19/0605 |
| | | | 123/299 |
| 8,555,702 B2* | 10/2013 | Sgatti et al. | 73/35.02 |
| 8,646,320 B2* | 2/2014 | Sasai | 73/114.38 |
| 8,789,514 B2* | 7/2014 | Caretta et al. | 123/486 |
| 8,820,151 B2* | 9/2014 | Ito | F02D 41/0025 |
| | | | 73/114.38 |
| 9,046,048 B2* | 6/2015 | Malaczynski et al. | |
| 2002/0152985 A1* | 10/2002 | Wolff | 123/305 |
| 2009/0198456 A1 | 8/2009 | Tsutsumi et al. | |
| 2009/0299605 A1 | 12/2009 | Kweon et al. | |
| 2009/0326788 A1* | 12/2009 | Yuasa et al. | 701/104 |
| 2010/0088008 A1 | 4/2010 | Tanaka et al. | |
| 2011/0209533 A1 | 9/2011 | Yasuda | |

FOREIGN PATENT DOCUMENTS

| | | |
|---|---|---|
| JP | 2009-068406 A | 4/2009 |
| JP | 2009-074499 A | 4/2009 |
| JP | 2009-180174 A | 8/2009 |
| JP | 2009-243471 A | 10/2009 |

* cited by examiner

CETANE NUMBER ESTIMATION DEVICE

CROSS REFERENCE TO RELATED APPLICATIONS

This application is a National Stage of International Application No. PCT/JP2011/057806 filed Mar. 29, 2011, the contents of all of which are incorporated herein by reference in their entirety.

FIELD OF THE DISCLOSURE

The present invention relates to a cetane number estimation device for estimating the cetane number of fuel supplied to a diesel engine.

BACKGROUND OF THE DISCLOSURE

In diesel engines, fuel injected through a fuel injection valve into a cylinder is ignited when a predetermined period of time has elapsed after the injection (this is referred to as an ignition delay). In order to improve the output and emission performances of diesel engines, control devices are widely employed to control the execution modes of engine control, such as timing and amount of fuel injection, upon consideration of such an ignition delay.

Diesel engines undergo a longer ignition delay as fuel having a lower cetane number is used. For this reason, even if the execution modes of engine control may have been set before shipping of diesel engines, for example, assuming the situation where fuel having a standard cetane number is used, fuel having a relatively low cetane number such as fuel for winter use, when supplied to a fuel tank, would have delayed ignition timing and undergo a poor combustion state, which may result in a misfire.

To avoid such an inconvenience, it is desirable to correct the execution modes of engine control based on the actual cetane number of fuel injected into a cylinder. It is then necessary to accurately estimate the cetane number of the fuel to make such a correction in a favorable manner.

Patent Document 1 has proposed a conventional device for injecting a small amount of fuel through a fuel injection valve and detecting an index value of an engine torque produced as a result of the fuel injection to estimate the cetane number of the fuel based on the index value. Focusing on the fact that the engine torque produced as a result of the injection of a predetermined amount of fuel varies depending on the cetane number of the fuel, the device is configured to estimate the cetane number of the fuel based on an index value of an engine torque produced as a result of the fuel injection.

PRIOR ART DOCUMENT

Patent Document

Patent Document 1
Japanese Laid-Open Patent Publication No. 2009-180174

SUMMARY OF THE INVENTION

Problems that the Invention is to Solve

Even if the same fuel injection valve may be opened in the same driving manner, the amount of fuel injected through the fuel injection valve may be different because the fuel pressure in a fuel supply passage for supplying fuel to the fuel injection valve may fluctuate or the fuel injection valve may actually operate in a slightly different manner. Such a variation in the amount of fuel injection also leads to a variation in the engine torque produced as a result of the fuel injection, which can disadvantageously contribute to a reduction in the accuracy of fuel cetane number estimation described above.

Accordingly, it is an objective of the present invention to provide a cetane number estimation device capable of accurately estimating the cetane number of fuel supplied to a diesel engine.

Means for Solving the Problems

To achieve the foregoing objective, and in accordance with one aspect of the present invention, a cetane number estimation device performs a fuel injection for estimation of the cetane number of fuel supplied to a diesel engine through drive control of a fuel injection valve based on a target amount of fuel injection and detects an index value of an output torque of the diesel engine produced as a result of the fuel injection to estimate the cetane number of the fuel based on the detected index value.

Upon such cetane number estimation, the greater the difference between the target amount of fuel injection and the actual amount of fuel injection, that is, the error in the amount of injection, the greater the error in the engine torque produced as a result of the fuel injection also becomes. Thus, the cetane number of the fuel can only be estimated at low accuracy based on an index value of the engine torque of the moment.

In the above described device, the actual amount of fuel injection through the fuel injection valve is detected. When the difference between the actual amount of fuel injection and the target amount of fuel injection is equal to or greater than a determination value, that is, when the error in the amount of injection is great and thereby the accuracy of fuel cetane number estimation is likely to decrease, the execution of estimation of the cetane number is limited. This reduces the influence of estimation of the cetane number of the fuel at low accuracy and thus allows the cetane number of the fuel to be estimated accurately.

In accordance with a form of the present invention, the execution limiting unit inhibits the execution of estimation of the cetane number by the estimating unit. In accordance with the thus configured device, reducing the chances of estimation of the cetane number of the fuel supplied to the diesel engine being executed at low accuracy is possible. It is therefore possible to prevent the accuracy of fuel cetane number estimation from being reduced.

In accordance with a preferable form, the detecting unit has a pressure sensor for detecting a fuel pressure serving as an index of the fuel pressure inside the fuel injection valve and detects the actual amount of fuel injection based on the manner in which the fuel pressure detected by the pressure sensor fluctuates. Fuel injection through the fuel injection valve causes a temporal reduction in the fuel pressure inside the fuel injection valve. Monitoring how the fuel pressure fluctuates in the device allows the actual amount of fuel injection to be detected accurately.

In accordance with another form of the present invention, the pressure sensor is mounted on the fuel injection valve. Compared to devices in which the fuel pressure is detected using a pressure sensor provided at a position away from a fuel injection valve, this arrangement allows for detection of the fuel pressure at a portion near the injection hole of the fuel injection valve. It is therefore possible to accurately detect the fuel pressure inside the fuel injection valve, which fluctuates in connection with the opening and closing operations of the fuel injection valve, using the pressure sensor and to accurately calculate the actual amount of fuel injection based on the fluctuation waveform of the fuel pressure detected using the pressure sensor.

In accordance with a further form of the present invention, the estimating unit executes estimation of the cetane number on the condition that the fuel injection for operation of the diesel engine is stopped.

DETAILED DESCRIPTION OF THE PREFERRED EMBODIMENTS

First Embodiment

A cetane number estimation device according to a first embodiment of the present invention will hereinafter be described.

Figure 1:
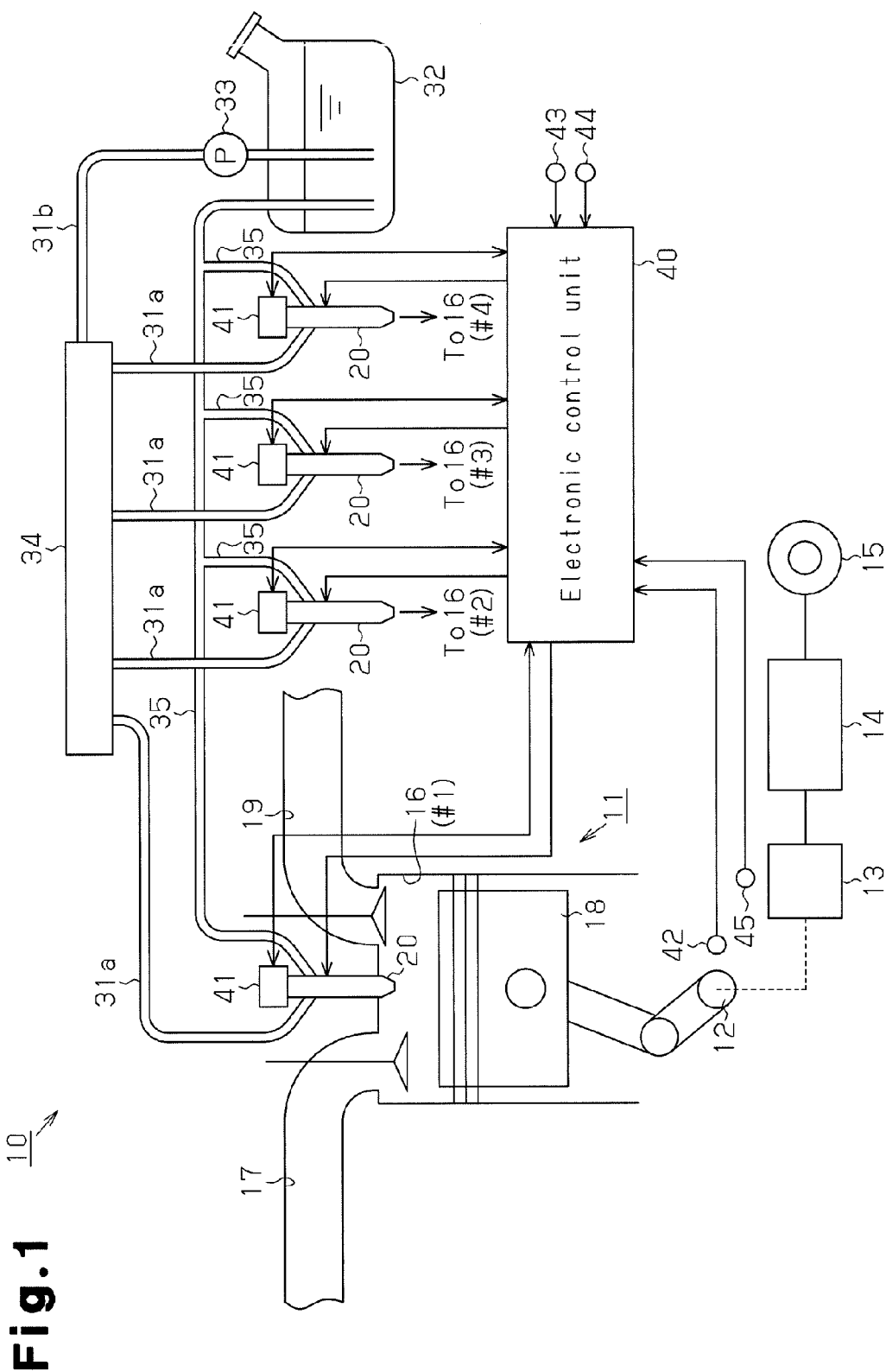
FIG. 1 is a schematic diagram showing the structure of a cetane number estimation device according to a first embodiment of the present invention.

As shown in FIG. 1, a vehicle 10 is equipped with a diesel engine 11 as a drive source. A crankshaft 12 of the diesel engine 11 is connected to wheels 15 via a clutch mechanism 13 and a manual transmission 14. When a passenger in the vehicle 10 operates a clutch operation member (e.g. clutch pedal), it results in an operating state of the clutch mechanism 13 where the crankshaft 12 and the manual transmission 14 are disconnected.

An intake passage 17 is connected to a cylinder 16 of the diesel engine 11. Air is taken into the cylinder 16 of the diesel engine 11 via the intake passage 17. The diesel engine 11 includes multiple (four in this embodiment [#1 to #4]) cylinders 16. The diesel engine 11 includes a direct injection type fuel injection valve 20 mounted on each cylinder 16 to inject fuel directly into the cylinder 16. Fuel injected when the fuel injection valve 20 is opened comes into contact with intake air compressed and heated in the cylinder 16 of the diesel engine 11 to be ignited and combusted. In the diesel engine 11, a piston 18 is pressed downward by energy produced as a result of the combustion of the fuel in the cylinder 16 and then the crankshaft 12 is rotated forcibly. Combustion gas after the combustion in the cylinder 16 of the diesel engine 11 is discharged as emissions into an exhaust passage 19 of the diesel engine 11.

The fuel injection valves 20 are connected separately to a common rail 34 via respective branch passages 31a, and the common rail 34 is connected to a fuel tank 32 via a supply passage 31b. A fuel pump 33 for pumping fuel is provided in the supply passage 31b. In this embodiment, fuel pumped and pressurized by the fuel pump 33 is stored in the common rail 34 and supplied into the respective fuel injection valves 20. A return passage 35 is connected to each of the fuel injection valves 20 and also connected to the fuel tank 32. Fuel inside the fuel injection valve 20 is partially returned to the fuel tank 32 via the return passage 35.

The internal structure of each fuel injection valve 20 will hereinafter be described.

Figure 2:
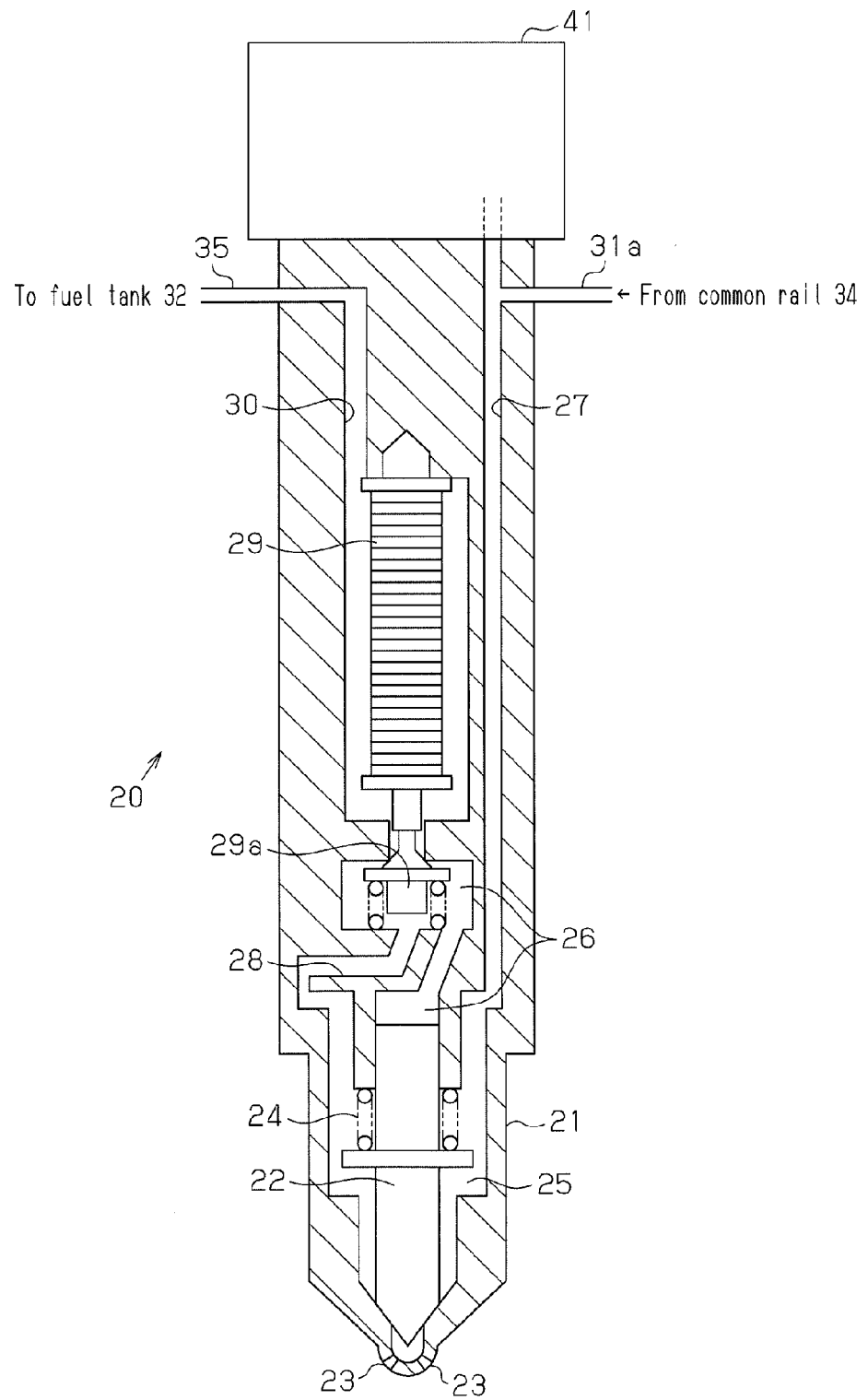
FIG. 2 is a cross-sectional view showing the cross-sectional structure of a fuel injection valve.

As shown in FIG. 2, a needle valve 22 is provided inside a housing 21 of each fuel injection valve 20. The needle valve 22 reciprocates within the housing 21 (vertically movable in the drawing). A spring 24 for constantly urging the needle valve 22 toward an injection hole 23 (downward in the drawing) is provided inside the housing 21. Also in the housing 21, a nozzle chamber 25 is formed on one side (lower side in the drawing) of the needle valve 22, while a pressure chamber 26 is formed on the other side (upper side in the drawing).

The nozzle chamber 25 is formed with multiple injection holes 23 that provide communications between the inside of the chamber and the outside of the housing 21 and is supplied with fuel from the corresponding branch passage 31a (common rail 34) through an introduction passage 27. The nozzle chamber 25 and the branch passage 31a (common rail 34) are connected to the pressure chamber 26 via a communication passage 28. The pressure chamber 26 is also connected to the return passage 35 (fuel tank 32) via a discharge passage 30.

The fuel injection valve 20 employs an electrically driven type valve, and a piezoelectric actuator 29 formed by stacking multiple piezoelectric elements (e.g. piezoelectric elements) that expand and contract when a drive signal is input is provided inside the housing 21. A valve element 29a is attached to the piezoelectric actuator 29 and provided inside the pressure chamber 26. One of the communication passage 28 (nozzle chamber 25) and the discharge passage 30 (return passage 35) is configured to come into selective communication with the pressure chamber 26 by operation of the piezoelectric actuator 29 and therefore movement of the valve element 29a.

In the fuel injection valve 20, the piezoelectric actuator 29, when a valve closing signal is input thereto, contracts and thereby the valve element 29a moves to provide communication between the communication passage 28 and the pressure chamber 26, while blocking communication between the return passage 35 and the pressure chamber 26. This provides communication between the nozzle chamber 25 and the pressure chamber 26 while inhibiting fuel in the pressure chamber 26 from being discharged into the return passage 35 (fuel tank 32). As a result, the pressure difference between the nozzle chamber 25 and the pressure chamber 26 becomes extremely small, and thereby, the needle valve 22 moves to close the injection hole 23 by the urging force of the spring 24, where the fuel injection valve 20 is in a state (closed state) of injecting no fuel.

On the other hand, the piezoelectric actuator 29, when a valve opening signal is input thereto, expands and thereby the valve element 29a moves to block communication between the communication passage 28 and the pressure chamber 26, while providing communication between the return passage 35 and the pressure chamber 26. This causes fuel in the pressure chamber 26 to be partially returned to the fuel tank 32 through the return passage 35 while inhibiting fuel outflow from the nozzle chamber 25 to the pressure chamber 26. As a result, the fuel pressure in the pressure chamber 26 decreases and thereby the pressure difference between the pressure chamber 26 and the nozzle chamber 25 increases. This pressure difference causes the needle valve 22 to move away from the injection hole 23 against the urging force of the spring 24, where the fuel injection valve 20 is in a state (opened state) of injecting fuel.

A pressure sensor 41 configured to output a signal according to the fuel pressure PQ inside the introduction passage 27 is mounted integrally on the fuel injection valve 20. Thus, compared to devices in which the fuel pressure is detected at a position away from the fuel injection valve 20 such as inside the common rail 34 (see FIG. 1), the fuel pressure can be detected at a portion near the injection hole 23 of the fuel injection valve 20, so that the change in the fuel pressure inside the fuel injection valve 20 associated with the opening of the fuel injection valve 20 can be detected accurately. One such pressure sensor 41 is provided for each fuel injection valve 20, that is, for each cylinder 16 of the diesel engine 11.

As shown in FIG. 1, the diesel engine 11 is provided with various sensors as peripheral devices for detecting an operating state. In addition to the pressure sensor 41, one of such sensors is, for example, a crank sensor 42 provided to detect the rotational phase and rotational speed (engine rotational speed NE) of the crankshaft 12. There are further provided, for example, an acceleration sensor 43 for detecting the operation amount (acceleration operation amount ACC) of an acceleration operation member (e.g. accelerator pedal), a vehicle speed sensor 44 for detecting the travel speed of the vehicle 10, and a clutch switch 45 for detecting whether or not the clutch operation member is operated.

One of such peripheral devices of the diesel engine 11 is, for example, an electronic control unit 40 provided to include a microcomputer. The electronic control unit 40 is configured to receive output signals from the various sensors, perform various arithmetic operations based on the output signals, and perform various controls associated with the operation of the diesel engine 11 such as drive control (fuel injection control) of the fuel injection valve 20 according to results of the arithmetic operations. In this embodiment, the electronic control unit 40 serves as an estimating unit, a detecting unit, and an execution limiting unit.

The fuel injection control of this embodiment is performed basically as follows.

A control target value of the amount of fuel injection (required injection amount TAU) for the operation of the diesel engine 11 is first calculated based on, for example, the acceleration operation amount ACC and the engine rotational speed NE. Next, a control target value of the timing of fuel injection (required injection timing Tst) and a control target value of the time of fuel injection (required injection duration Ttm) are calculated based on the required injection amount TAU and the engine rotational speed NE. The respective fuel injection valves 20 are then driven to open based on the required injection timing Tst and the required injection duration Ttm. This causes fuel to be injected through the fuel injection valves 20 in an amount according to the operating state of the diesel engine 11 of the moment and supplied into each cylinder 16 of the diesel engine 11.

In the fuel injection control of this embodiment, when the travel speed of the vehicle 10 decreases and the engine rotational speed NE decreases to within a predetermined speed range as a result of stopping the operation of the acceleration operation member (i.e. the acceleration operation amount ACC=0), control (fuel cutoff control) is performed for temporarily stopping the fuel injection for the operation of the diesel engine 11.

Further, in the fuel injection control of this embodiment, two regions, lower (lower cetane number region) and higher (higher cetane number region) in the fuel cetane number, are set and the fuel injection control is performed in a different execution mode for each of the regions. For example, the required injection timing Tst is set to be advanced in the lower cetane number region than in the higher cetane number region. More specifically, in this embodiment, the relationship between the engine operating state defined based on the required injection amount TAU and the engine rotational speed NE and the required injection timing Tst according to the lower cetane number region has been obtained preliminarily based on results of various experiments and simulations and stored in the electronic control unit 40 as a calculation map ML. In the lower cetane number region, the required injection timing Tst is calculated from the calculation map ML based on the required injection amount TAU and the engine rotational speed NE. Similarly, the relationship between the engine operating state defined based on the required injection amount TAU and the engine rotational speed NE and the required injection timing Tst according to the higher cetane number region has been obtained preliminarily based on results of various experiments and simulations and stored in the electronic control unit 40 as a calculation map MH. In the higher cetane number region, the required injection timing Tst is calculated from the calculation map MH based on the required injection amount TAU and the engine rotational speed NE.

In the thus performed fuel injection through the fuel injection valve 20, errors may be observed in the injection timing and/or injection amount due to, for example, initial individual variability and/or variation over time of the fuel injection valve 20. Such errors can undesirably cause a change in the output torque of the diesel engine 11. To address the problem in such a manner so as to properly perform the fuel injection through the fuel injection valves 20 according to the operating state of the diesel engine 11, in this embodiment, correction processing is performed in which the detection time waveform of the fuel injection rate is formed based on the fuel pressure PQ detected using the pressure sensor 41 and the required injection timing Tst and the required injection duration Ttm are corrected based on the detection time waveform. This correction processing is performed separately for each cylinder 16 of the diesel engine 11.

The fuel pressure inside the fuel injection valve 20 fluctuates in connection with the opening and closing operations of the fuel injection valve 20, that is, decreases in connection with the opening of the fuel injection valve 20 and subsequently increases with the closing of the fuel injection valve 20. It is therefore possible to accurately figure out the actual operating characteristics (e.g. the actual amount of fuel injection, the timing when the valve starts opening, and the timing when the valve starts closing) of the fuel injection valve 20 by monitoring the fluctuation waveform of the fuel pressure inside the fuel injection valve 20 when the fuel injection is performed. It is accordingly possible to accurately set the fuel injection timing and the fuel injection amount according to the operating state of the diesel engine 11 by correcting the required injection timing Tst and the required injection duration Ttm based on the actual operating characteristics of the fuel injection valve 20.

The correction processing will hereinafter be described in detail.

First will be described a procedure for forming a manner in which the fuel pressure fluctuates (detection time waveform of the fuel injection rate in this embodiment) when the fuel injection is performed.

Figure 3:
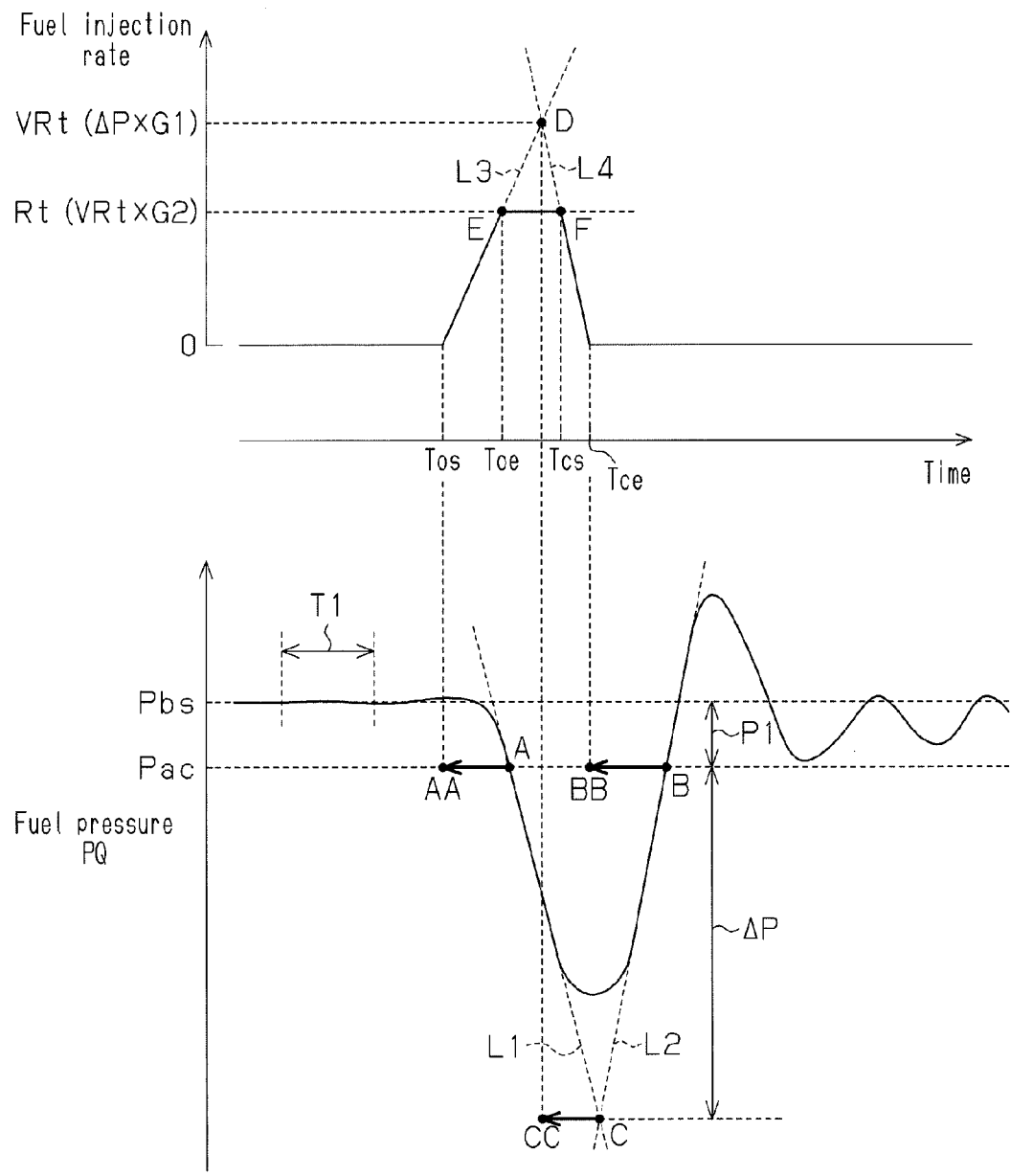
FIG. 3 is a timing chart showing the relationship between changes in the fuel pressure and the detection time waveform of the fuel injection rate.

FIG. 3 shows the relationship between changes in the fuel pressure PQ and the detection time waveform of the fuel injection rate.

As shown in FIG. 3, in this embodiment, the timing when the fuel injection valve 20 starts opening operation (specifically, when the needle valve 22 starts moving toward the open side) (valve opening operation start time Tos), the timing when the fuel injection rate reaches its peak (maximum injection rate arrival time Toe), the timing when the fuel injection rate starts decreasing (injection rate decrease start time Tcs), and the timing when the fuel injection valve 20 finishes closing operation (specifically, when the needle valve 22 finishes moving toward the close side) (valve closing operation completion time Tce) are detected, respectively.

An average value of the fuel pressure PQ is first calculated for a predetermined period of time T1 immediately before the fuel injection valve 20 starts opening operation and stored as a reference pressure Pbs. The reference pressure Pbs is used as a pressure that corresponds to the fuel pressure inside the fuel injection valve 20 when closed.

Next, a predetermined pressure P1 is subtracted from the reference pressure Pbs to calculate an operating pressure Pac (Pac=Pbse−P1). The predetermined pressure P1 corresponds to a change in the fuel pressure PQ while the needle valve 22 is in a close position when the fuel injection valve 20 is driven to open or close, that is, to a change in the fuel pressure PQ not contributing to the movement of the needle valve 22.

Subsequently, a first-order differential value d(PQ)/dt of the fuel pressure PQ in a period when the fuel pressure PQ decreases immediately after the start of the fuel injection is calculated. A tangent L1 to the time waveform of the fuel pressure PQ is then obtained at the point where the first-order differential value has a minimum value, that is, the fuel pressure PQ has a maximum downward inclination, and an intersection A of the tangent L1 and the operating pressure Pac is calculated. The intersection A is shifted backward by the following detection delay of the fuel pressure PQ to obtain a point AA to which the valve opening operation start time Tos is identified to correspond. The detection delay corresponds to a delay in timing of the change in the fuel pressure PQ to the change in the pressure inside the nozzle chamber 25 of the fuel injection valve 20 (see FIG. 2), which occurs due to, for example, the distance between the nozzle chamber 25 and the pressure sensor 41.

A first-order differential value of the fuel pressure PQ in a period when the fuel pressure PQ decreases once immediately after start of fuel injection and then, increases is calculated. A tangent L2 to the time waveform of the fuel pressure PQ is then obtained at the point where the first-order differential value has a maximum value, that is, the fuel pressure PQ has a maximum upward inclination, and an intersection B of the tangent L2 and the operating pressure Pac is calculated. The intersection B is shifted backward by the detection delay to obtain a point BB to which the valve closing operation completion time Tce is identified to correspond.

Further, an intersection C of the tangents L1 and L2 is calculated, and the difference between the fuel pressure PQ and the operating pressure Pac (hypothetical pressure reduction ΔP [ΔP=Pac−PQ]) is obtained at the intersection C. The hypothetical pressure reduction ΔP is then multiplied by a gain G1 set based on the required injection amount TAU to obtain a hypothetical maximum fuel injection rate VRt (VRt=ΔP×G1). The hypothetical maximum fuel injection rate VRt is further multiplied by a gain G2 set based on the required injection amount TAU to obtain a maximum injection rate Rt (Rt=VRt×G2).

Subsequently, the intersection C is shifted backward by the detection delay to obtain a time point CC, to which the hypothetical maximum fuel injection rate VRt is identified to correspond as a point D. Then, the time point of an intersection E of a straight line L3 connecting the point D and the valve opening operation start time Tos (specifically, the point where the fuel injection rate is 0 at the time Tos) and the maximum injection rate Rt is identified as the maximum injection rate arrival time Toe.

Also, the time point of an intersection F of a line L4 connecting the point D and the valve closing operation completion time Tce (specifically, the point where the fuel injection rate is 0 at the time Tce) and the maximum injection rate Rt is identified as the injection rate decrease start time Tcs.

Further, the trapezoidal time waveform formed by the valve opening operation start time Tos, the maximum injection rate reach time Toe, the injection rate decrease start time Tcs, and the valve closing operation completion time Tce is used as a detection time waveform for the fuel injection rate of the fuel injection.

Next will be described in detail, with reference to FIGS. 4 and 5, a procedure for correcting (performing correction processing for) the various control target values of fuel injection control based on the detection time waveform.

Figure 4:
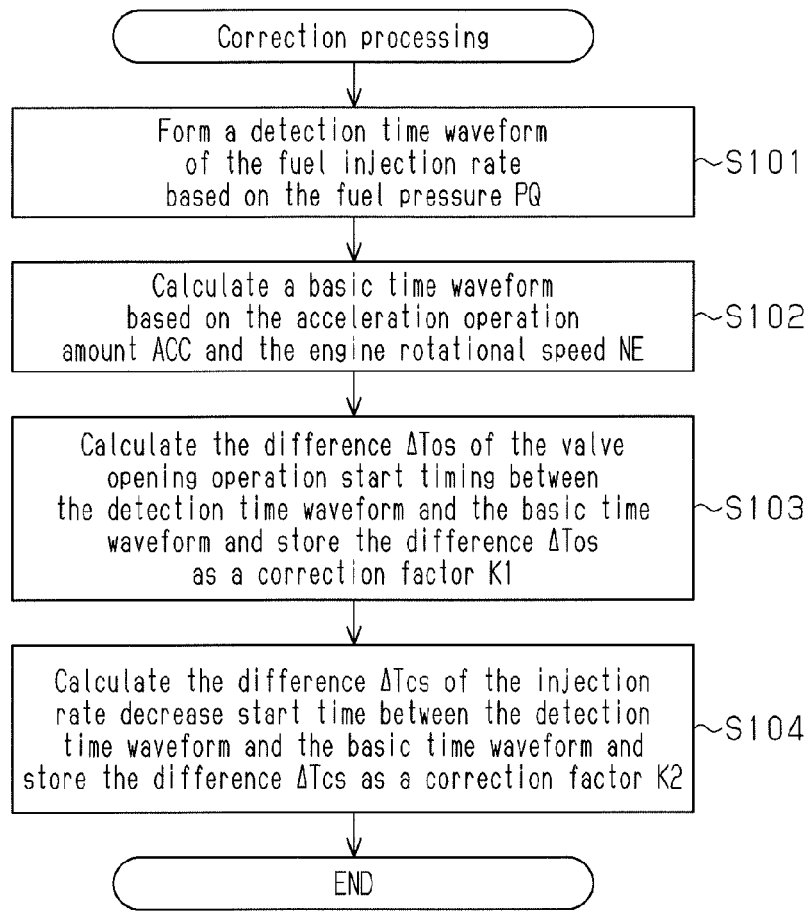
FIG. 4 is a flowchart showing a procedure for performing a correction processing.

FIG. 4 is a flowchart specifically showing a procedure for the correction processing. A series of processing shown in this flowchart conceptually shows a procedure for performing the correction processing. The actual processing is performed by the electronic control unit 40 as interrupt processing at every predetermined period. FIG. 5 shows an example of the relationship between the detection time waveform and the following basic time waveform.

As shown in FIG. 4, in this correction processing, first, a detection time waveform when the fuel injection is performed is formed based on the fuel pressure PQ as mentioned above (step S101). In addition, based on the operating state of the diesel engine 11, including the acceleration operation amount ACC and the engine rotational speed NE, a basic value (basic time waveform) is set for the time waveform of the fuel injection rate when the fuel injection is performed (step S102). In this embodiment, the relationship between the operating state of the diesel engine 11 and a basic time waveform suitable for the operating state has been obtained preliminarily based on results of experiments and simulations and stored in the electronic control unit 40. In the processing of step S102, a basic time waveform is set from the relationship based on the operating state of the diesel engine 11 of the moment.

Figure 5:
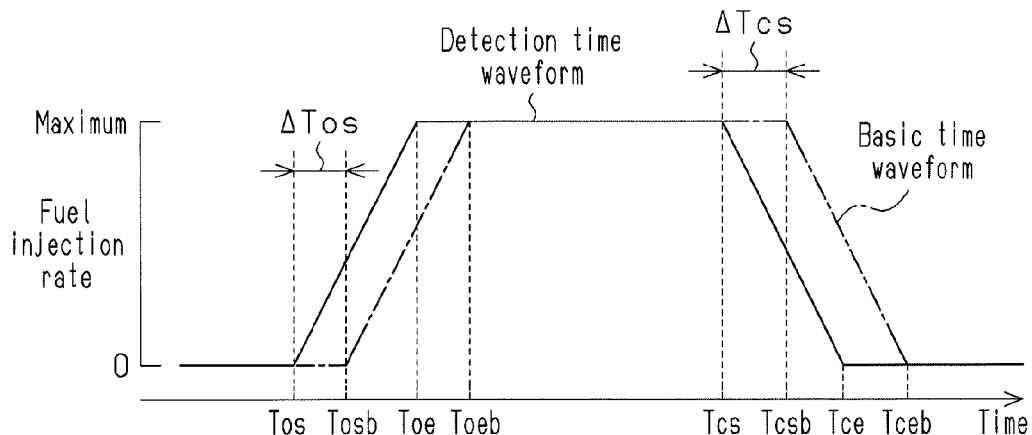
FIG. 5 is a timing chart showing an example of the relationship between the detection time waveform and the basic time waveform.

As shown in FIG. 5, a trapezoidal time waveform defined by the valve opening operation start time Tosb, the maximum injection rate arrival time Toeb, the injection rate reduction start time Tcsb, the valve closing operation completion time Tceb, and the maximum injection rate is set as the basic time waveform (indicated by a line formed by a long dash alternating with a short dash).

The basic time waveform and the detection time waveform (indicated by the solid line) are compared and, based on a result of the comparison, correction terms K1 and K2 are calculated, respectively, for correcting the control target value of the timing to start the fuel injection (the required injection timing Tst) and the control target value of the period of time to perform the fuel injection (the required injection duration Ttm). Specifically, the difference ΔTos (ΔTos=Tosb−Tos) between the valve opening operation start time Tosb in the basic time waveform and the valve opening operation start time Tos in the detection time waveform is calculated and stored as the correction factor K1 (step S103 of FIG. 4). The difference ΔTcs (ΔTcs=Tcsb−Tcs) between the injection rate decrease start time Tcsb (FIG. 5) in the basic time waveform and the injection rate decrease start time Tcs in the detection time waveform is also calculated and stored as the correction factor K2 (step S104 of FIG. 4).

After the correction factors K1 and K2 are thus calculated, the processing is temporarily suspended.

Upon fuel injection control, the required injection timing Tst is corrected by the correction factor K1 (the required injection timing Tst is added with the correction factor K1 in this embodiment) and the corrected value is calculated as a final required injection timing Tst. Thus calculating the required injection timing Tst allows the difference between the valve opening operation start time Tosb in the basic time waveform and the valve opening operation start time Tos in the detection time waveform to be reduced, whereby the timing to start the fuel injection can be set accurately according to the operating state of the diesel engine 11.

The required injection duration Ttm is also corrected by the correction factor K2 (the required injection duration Ttm is added with the correction factor K2 in this embodiment) and the corrected value is calculated as a final required injection duration Ttm. Thus calculating the required injection duration Ttm allows the difference between the injection rate decrease start time Tcsb in the basic time waveform and the injection rate decrease start time Tcs in the detection time waveform to be reduced, whereby the timing when the fuel injection rate of the fuel injection starts decreasing can be set accurately according to the operating state of the diesel engine 11.

In this embodiment, since the required injection timing Tst and the required injection duration Ttm are thus corrected based on the difference between the actual operating characteristics (specifically, the detection time waveform) of the fuel injection valve 20 and the predefined basic operating characteristics (specifically, the basic time waveform), the difference between the actual operating characteristics of the fuel injection valve 20 and the basic operating characteristics (operating characteristics of fuel injection valves having standard properties) is reduced. This allows the timing and amount of fuel injection through the respective fuel injection valves 20 to be set properly according to the operating state of the diesel engine 11.

The cetane number estimation device of this embodiment executes control (estimation control) of the cetane number of fuel supplied for combustion in the diesel engine 11. The estimation control will hereinafter be outlined.

In the estimation control, execution conditions are set including that the fuel cutoff control is performed ([condition 1] to be described hereinafter). When the execution conditions are met, a predetermined small amount FQ (e.g. a few cubic millimeters) of fuel is injected into the diesel engine 11 and an index value (rotational fluctuation amount ΣΔNE to be described hereinafter) for an output torque of the diesel engine 11 produced as a result of the fuel injection is detected and, based on the rotational fluctuation amount ΣΔNE, the cetane number of the fuel is estimated. That the higher the output torque of the diesel engine 11, the greater the rotational fluctuation amount ΣΔNE.

Fuel supplied to the diesel engine 11, if having a higher cetane number, is ignited more easily and less likely to remain uncombusted, and accordingly combustion of such fuel generates a higher engine torque. In the estimation control of this embodiment, based on the relationship between the cetane number of such fuel and the output torque of the diesel engine 11, the cetane number of the fuel is estimated.

Even if the same fuel injection valve 20 may be opened in the same driving manner, the amount of fuel injected through the fuel injection valve 20 cannot be the same. Such a variation in the amount of fuel injection occurs because the fuel pressure in a fuel supply passage (specifically including the branch passages 31a, the supply passage 31b, and the common rail 34 shown in FIG. 1) for supplying high-pressure fuel to the fuel injection valves 20 may fluctuate and/or the fuel injection valves 20 may actually operate in a different manner, etc. Such a variation in the amount of fuel injection also leads to a variation in the engine torque (specifically, the rotational fluctuation amount ΣΔNE) produced as a result of the injection of a predetermined amount FQ of fuel, which can disadvantageously contribute to a reduction in the accuracy of fuel cetane number estimation upon execution of the estimation control.

Figure 6:
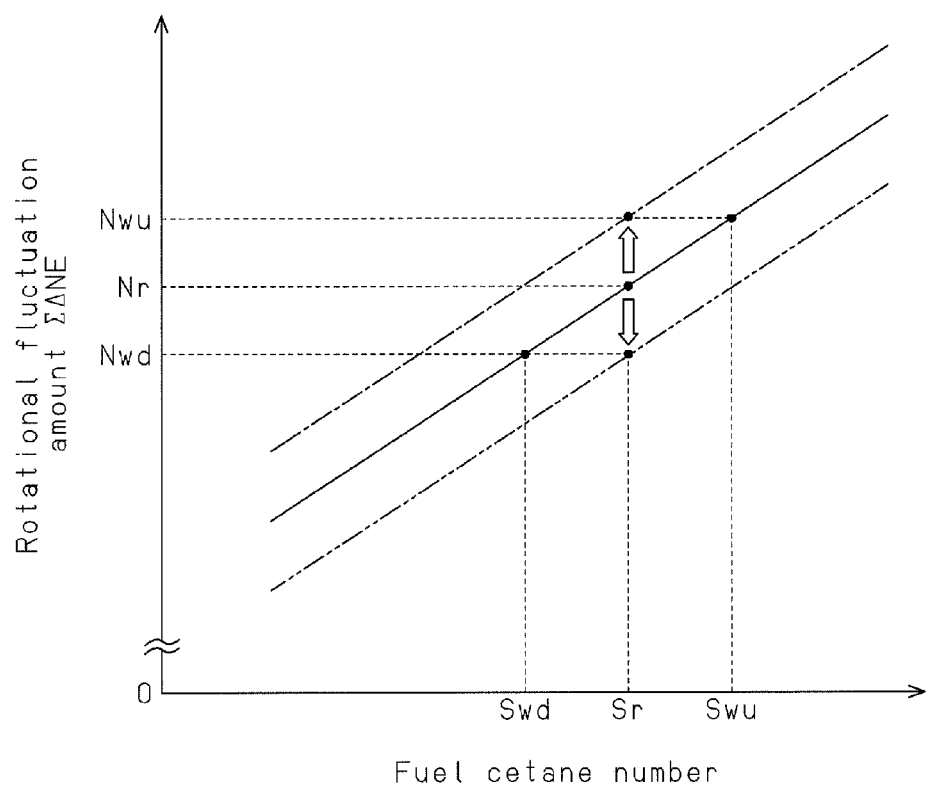
FIG. 6 is a graph showing the relationship between the rotational fluctuation amount and the fuel cetane number.

More specifically, if the target amount of fuel injection (the predetermined amount FQ in this embodiment) equals the actual amount of fuel injection, the relationship between the rotational fluctuation amount ΣΔNE and the fuel cetane number is, for example, indicated by the solid line in FIG. 6. In the specific example shown in the drawing, the rotational fluctuation amount ΣΔNE is detected as "Nr" when the actual fuel cetane number is "Sr". In this case, the rotational fluctuation amount ΣΔNE is detected according to the actual fuel cetane number.

Compared to this, if the actual amount of fuel injection is greater than the target amount of fuel injection amount, the diesel engine 11 has an accordingly high output torque and thus the rotational fluctuation amount ΣΔNE also has a high value as indicated by the line formed by a long dash alternating with a short dash in FIG. 6. In the specific example shown in the drawing, the rotational fluctuation amount ΣΔNE is detected as "Nwu" according to a cetane number "Swu" higher than the actual cetane number "Sr", although it should be detected as "Nr" because the actual fuel cetane number is "Sr".

On the other hand, if the actual amount of fuel injection is smaller than the target amount of fuel injection, the diesel engine 11 has an accordingly low output torque and thus the rotational fluctuation amount ΣΔNE also has a low value as indicated by the broken line in which a long dash alternates with a pair of short dashes in FIG. 6. In the specific example shown in the drawing, the rotational fluctuation amount ΣΔNE is detected as "Nwd" according to a cetane number "Swd" lower than the actual cetane number "Sr", although it should be detected as "Nr" because the actual fuel cetane number is "Sr."

Therefore, upon such fuel cetane number estimation, the greater the difference between the target amount of fuel injection and the actual amount of fuel injection, that is, the error in the amount of injection, the greater the error in the engine torque produced as a result of the injection of a predetermined amount FQ of fuel also becomes, whereby the cetane number of the fuel can only be estimated at low accuracy based on an index value (rotational fluctuation amount ΣΔNE) for the engine torque of the moment.

In this embodiment, a small amount (the predetermined amount FQ) of fuel is injected for estimation of the cetane number of the fuel. In such a case where only a small amount of fuel injection is required, the degree of change in the engine torque when an error in the amount of injection occurs is likely to become high, which can easily give rise to a reduction in the accuracy of fuel cetane number estimation based on the rotational fluctuation amount ΣΔNE.

In consideration of these circumstances, in this embodiment, the actual fuel injection amount RQ is first detected upon fuel cetane number estimation. The actual fuel injection amount RQ can be detected accurately based on the detection time waveform illustrated in FIG. 3. If the difference between the actual fuel injection amount RQ and the target amount of fuel injection (the predetermined amount FQ) is equal to or greater than a determination value J, that is, the accuracy of fuel cetane number estimation is likely to decrease, the execution of estimation of the cetane number is inhibited.

It is therefore possible to execute estimation of the cetane number of the fuel supplied to the diesel engine 11 only in the case where the estimation can be executed at high accuracy. Accordingly, reducing the chances of estimation of the cetane number of the fuel being executed at low accuracy is possible, whereby it is possible to estimate the cetane number accurately.

A procedure for performing processing for estimation control (estimation control processing) will hereinafter be described in detail.

Figure 7:
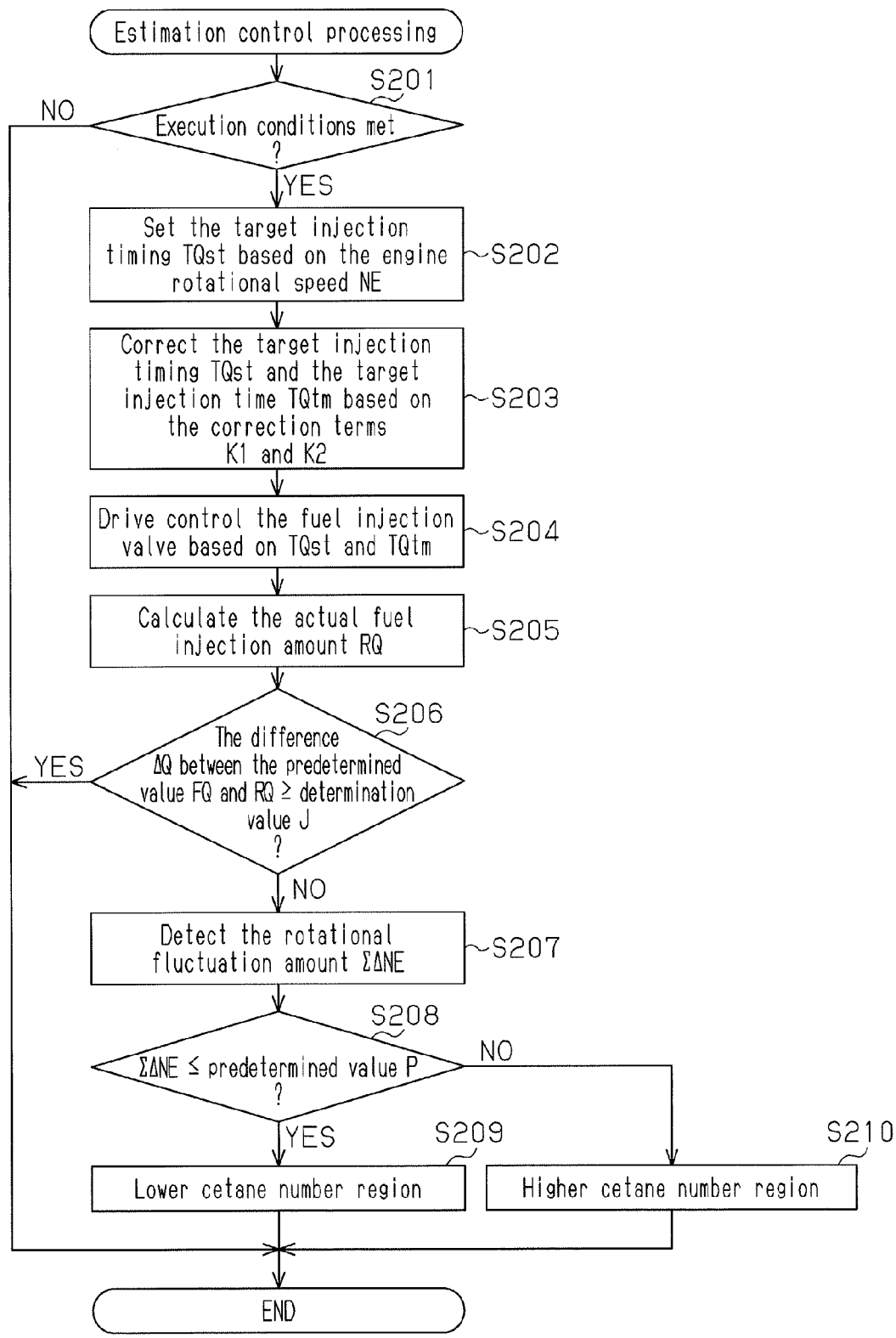
FIG. 7 is a flowchart showing a procedure for performing estimation control processing according to the first embodiment.

FIG. 7 is a flowchart showing a specific procedure for performing the estimation control processing. A series of processing shown in this flowchart conceptually shows a procedure for performing the estimation control processing. The actual processing is performed by the electronic control unit 40 as interrupt processing at every predetermined period.

As shown in FIG. 7, it is first determined in this processing whether or not execution conditions are met (step S201). In this step, it is determined that the execution conditions are met if the following [condition 1] to [condition 3] are all met.
[Condition 1] The fuel cutoff control is being performed.
[Condition 2] The clutch mechanism 13 is in an active state where the crankshaft 12 and the manual transmission 14 are disconnected. Specifically, the clutch operation member is being operated.
[Condition 3] The correction processing is performed properly. Specifically, the correction factors K1 and K2 calculated in the correction processing is neither the upper limit nor the lower limit.

If the above-described execution conditions are not met (NO in step S201), the processing is temporarily suspended without performing processing in the following steps S202 to S210.

Thereafter, when the processing is performed repeatedly and the execution conditions are met (YES in step S201), the processing for estimation of the fuel cetane number starts to be performed.

Specifically, a target injection timing TQst is first set from a calculation map MA based on the engine rotational speed NE. Even if the fuel injection for cetane number estimation may be performed with the same fuel cetane number and in the same fuel injection amount, the rotational fluctuation amount ΣΔNE has a lower value as the fuel injection timing is further delayed and the engine rotational speed NE is higher. This is considered to be due to the fact that as the fuel injection timing is further delayed and the engine rotational speed NE is higher, part of the fuel is combusted under the condition where the temperature and pressure in the cylinder 16 is lower and thus a substantial part remains uncombusted. For this reason, the fuel injection for cetane number estimation can be performed such that the variation in the rotational fluctuation amount ΣΔNE is reduced by setting the injection timing according to the engine rotational speed NE. In consideration of this point, in this embodiment, the injection timing is set based on the engine rotational speed NE. More specifically, the injection timing at which the variation in the rotational fluctuation amount ΣΔNE due to the difference in the engine rotational speed NE can be reduced is set as the target injection timing TQst. For example, the higher the engine rotational speed NE, the further delayed the injection timing is set. In this embodiment, the relationship between the target injection timing TQst and the engine rotational speed NE has been obtained preliminarily based on results of various experiments and simulations and stored in the calculation map MA.

Thereafter, the target injection timing TQst and the predefined control target value of the time of fuel injection (target injection time TQtm) are corrected by the correction factors K1 and K2 calculated in the correction processing described with reference to FIGS. 4 and 5 (step S203). More specifically, the correction factor K1 is added to the target injection timing TQst to set a new target injection timing TQst, while the correction factor K2 is added to the target injection time TQtm to set a new target injection time TQtm.

The driving of the fuel injection valve 20 is then controlled based on the target injection timing TQst and the target injection time TQtm and fuel injection is performed through the fuel injection valve 20 (step S204). Through such drive control of the fuel injection valve 20, a predetermined amount FQ of fuel is thus injected through the fuel injection valve 20 at the timing at which the variation in the rotational fluctuation amount ΣΔNE can be reduced. In this embodiment, the fuel injection in the processing of step S204 is performed using a predefined one of the multiple fuel injection valves 20 (the fuel injection valve 20 mounted on the cylinder 16 [#1] in this embodiment). Similarly, the correction values K1 and K2 used in the processing employ values correspondingly calculated to a predefined one of the fuel injection valves 20 (the fuel injection valve 20 mounted on the cylinder 16 [#1] in this embodiment).

Thereafter, a detection time waveform when the fuel injection valve 20 is driven and opened is formed as shown in FIG. 3 and, based on the detection time waveform, an actual fuel injection amount RQ is calculated as shown in FIG. 5 (step S205). In this embodiment, a value corresponding to the area surrounded by the line on which the fuel injection rate (see FIG. 5) is 0 and the detection time waveform is calculated as the actual fuel injection amount RQ.

It is then determined whether or not the difference ΔQ between the actual fuel injection amount RQ and the predetermined amount FQ (specifically, the absolute value of [RQ−FQ]) is equal to or greater than the determination value J (step S206). As for the determination value J, a value (e.g. a fraction of the predetermined amount FQ) with which it is possible to properly determine whether or not the accuracy of fuel cetane number estimation can be maintained high has been obtained preliminarily based on results of various experiments and simulations and stored in the electronic control unit 40.

If the difference ΔQ is smaller than the determination value J (NO in step S206), it is determined that the accuracy of fuel cetane number estimation can be maintained high and the processing for estimation of the fuel cetane number is performed.

Figure 8:
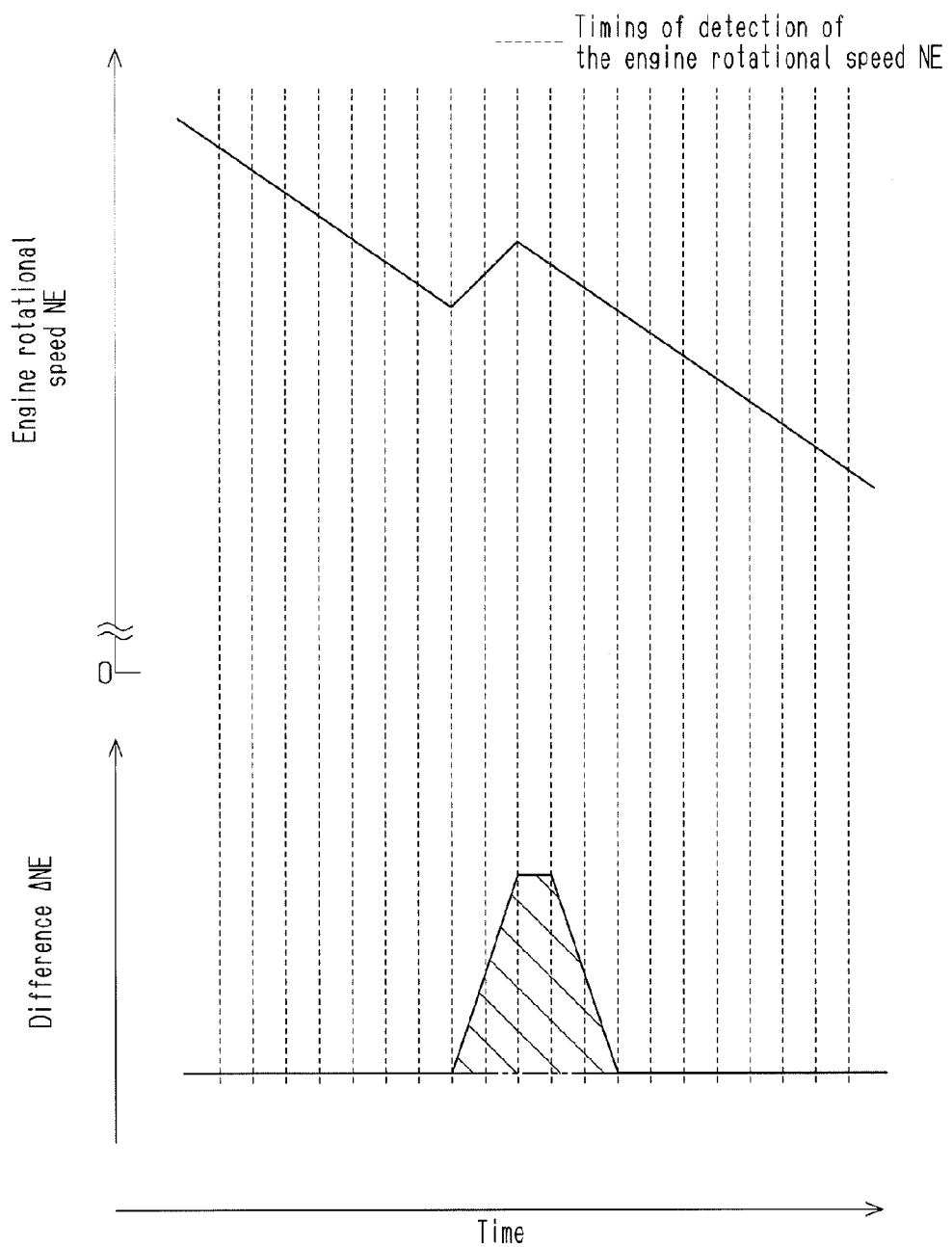
FIG. 8 is a diagram illustrating a method for calculating the rotational fluctuation amount.

That is, the rotational fluctuation amount ΣΔNE is first detected and stored as an index value of an output torque of the diesel engine 11 produced as a result of the fuel injection in the predetermined amount FQ (step S207). The rotational fluctuation amount ΣΔNE is specifically detected as follows. As shown in FIG. 8, in the device of this embodiment, the engine rotational speed NE is detected at predetermined time intervals and, for each detection, the difference ΔNE (ΔNE=NE−NEi) between the engine rotational speed NE and the predetermined nth engine rotational speed NEi prior to the current engine rotational speed NE (n is three in this embodiment) is calculated. An accumulated value of the change in the difference ΔNE associated with execution of the fuel injection (corresponding to the area of the shaded region in FIG. 8) is calculated and stored as the rotational fluctuation amount ΣΔNE. Changes in the engine rotational speed NE and the difference ΔNE shown in FIG. 8 are simplified for the sake of easy understanding of the method for calculating the rotational fluctuation amount ΣΔNE and therefore is slightly different from the actual change.

After the rotational fluctuation amount ΣΔNE is thus detected, it is determined whether or not the rotational fluctuation amount ΣΔNE is smaller than a predetermined value P (step S208 of FIG. 7). If the rotational fluctuation amount ΣΔNE is smaller than the predetermined value P (YES in step S208), it is determined that the cetane number of the fuel of the moment is within the lower cetane number region (step S209) and then the processing is temporarily suspended. After that, fuel injection control for the operation of the diesel engine 11 is performed in a manner suitable for fuel having a lower cetane number. That is, the required injection timing Tst is calculated from the calculation map ML based on the required injection amount TAU and the engine rotational speed NE.

On the other hand, if the rotational fluctuation amount ΣΔNE is equal to or greater than the predetermined value P (NO in step S208), it is determined that the cetane number of the fuel of the moment is within the higher cetane number region (step S210) and then the processing is temporarily suspended. After that, fuel injection control for the operation of the diesel engine 11 is performed in a manner suitable for fuel having a higher cetane number. That is, the required injection timing Tst is calculated from the calculation map MH based on the required injection amount TAU and the engine rotational speed NE.

If the difference ΔQ between the actual fuel injection amount RQ and the predetermined amount FQ is equal to or greater than the determination value J (YES in step S206), it is determined that the accuracy of fuel cetane number estimation is likely to decrease and the execution of estimation of the fuel cetane number is inhibited (the processing of steps S207 to S210 is skipped).

As described heretofore, this embodiment offers the following advantages.

(1) If the difference ΔQ between the predetermined amount FQ and the actual fuel injection amount RQ is equal to or greater than the determination value J, the execution of estimation of the fuel cetane number is inhibited. This allows reducing the chances of estimation of the fuel cetane number being executed at low accuracy, whereby it is possible to estimate the cetane number accurately.

(2) Since the pressure sensor 41 is provided for detecting the fuel pressure PQ inside the fuel injection valve 20, the actual fuel injection amount RQ can be detected accurately by monitoring how the fuel pressure detected by the pressure sensor 41 fluctuates.

(3) The pressure sensor 41 is mounted integrally on the fuel injection valve 20. Thus, compared to devices in which the fuel pressure is detected at a position away from the fuel injection valve 20 such as inside the common rail 34, the fuel pressure can be detected at a portion near the injection hole 23 of the fuel injection valve 20, so that the change in the fuel pressure inside the fuel injection valve 20 associated with the opening of the fuel injection valve 20 can be detected accurately.

Second Embodiment

A cetane number estimation device according to a second embodiment of the present invention will hereinafter be described with an emphasis on differences from the first embodiment.

The cetane number estimation device of this embodiment has the same structure as the cetane number estimation device of the above-described first embodiment and the details will not be described here.

The cetane number estimation device of this embodiment differs from the cetane number estimation device of the first embodiment in the manner of execution mode of the estimation control.

Specifically, in the estimation control of the first embodiment, if the difference ΔQ between the actual fuel injection amount RQ and the predetermined amount FQ is equal to or greater than the determination value J (YES in step S206 of FIG. 7), it is determined that the accuracy of fuel cetane number estimation is likely to decrease and the execution of estimation of the fuel cetane number is inhibited (the processing of steps S207 to S210 is skipped).

Figure 9:
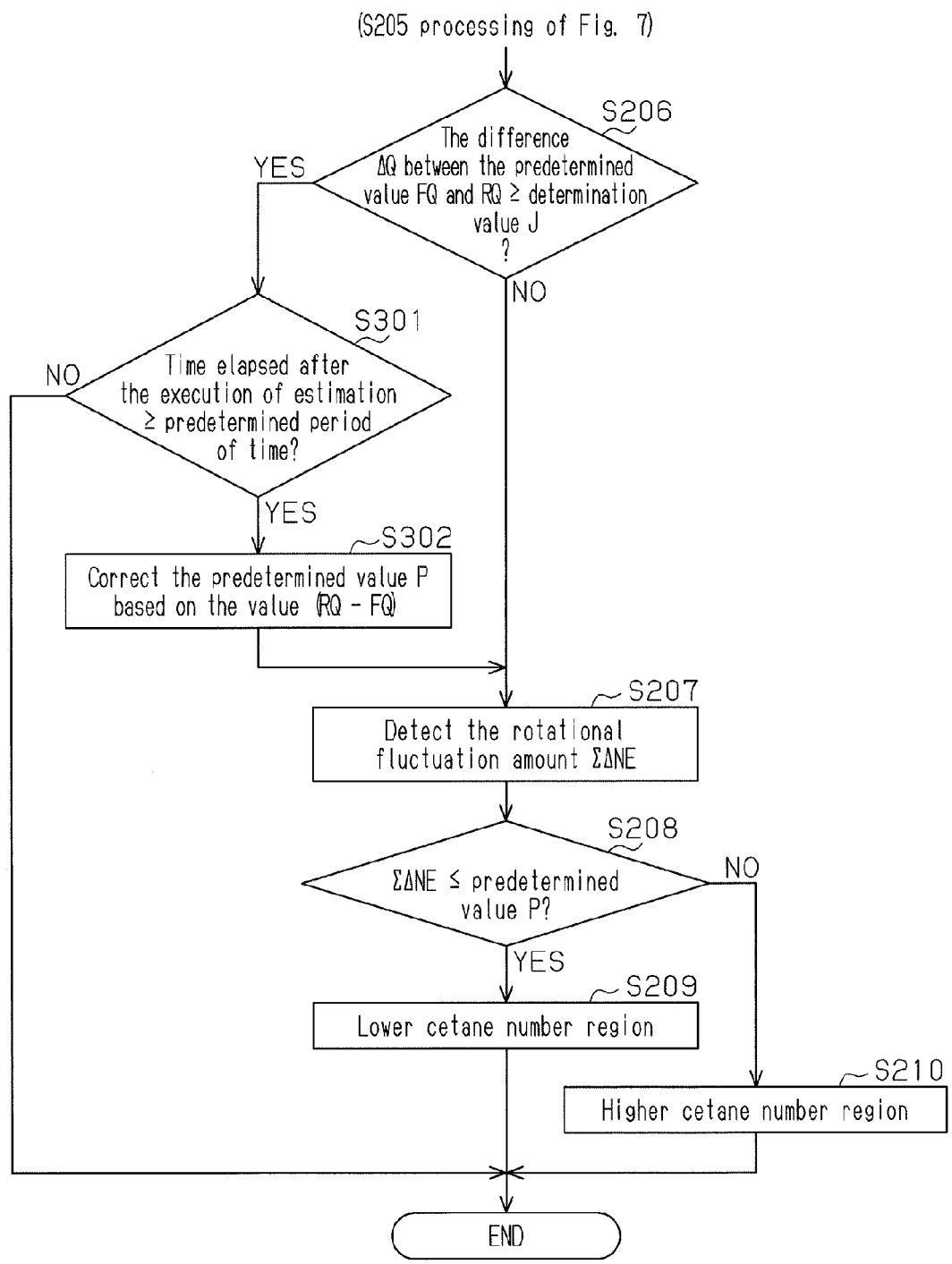
FIG. 9 is a flowchart showing a procedure for performing estimation control processing according to a second embodiment.

In contrast, in the estimation control of this embodiment, if the difference ΔQ between the actual fuel injection amount RQ and the predetermined amount FQ is equal to or greater than the determination value J (YES in step S206), it is determined whether or not a predetermined period of time or more has elapsed since the last execution of estimation of the fuel cetane number (step S301), as shown in FIG. 9.

Then, if the time elapsed after the last execution of estimation of the fuel cetane number is shorter than the predetermined period of time (NO in step S301), the execution of estimation of the fuel cetane number is inhibited (the processing of steps S207 to S210 is skipped), as is the case in the first embodiment.

On the other hand, if the time elapsed after the last execution of estimation of the fuel cetane number is equal to or longer than the predetermined period of time (YES in step S301), the processing for estimation of the fuel cetane number is performed (steps S207 to S210).

In this case, however, the predetermined value P is corrected before the processing of steps S207 to S210 based on a value (RQ−FQ) obtained by subtracting the predetermined amount FQ from the actual fuel injection amount RQ (step S302). Specifically, a corrected value KP is calculated from a calculation map MP based on the above-described value (RQ−FQ) and added to the predetermined value P (P+KP) to be stored as a new predetermined value P. In this embodiment, the relationship between the above-described value (RQ−FQ) and the corrected value KP with which the cetane number of the fuel can be estimated accurately has been obtained preliminarily based on results of various experiments and simulations and stored in the electronic control unit 40 as the calculation map MP. In the processing of step S302, the higher the value (RQ−FQ), the higher the predetermined value P is corrected to be, that is, to correspond to a higher cetane number. The thus corrected predetermined value P is then used to execute estimation of the fuel cetane number (steps S207 to S210).

Thus executing estimation of the fuel cetane number allows the predetermined value P to be corrected according to the error in the rotational fluctuation amount ΣΔNE due to an error in the amount of injection, although it may be great in this case (see the outlined arrows in FIG. 6). Based on the predetermined value P, it is therefore possible to accurately estimate whether the cetane number of the fuel supplied to the diesel engine 11 is within the lower cetane number region or the higher cetane number region.

Thus, in the estimation control of this embodiment, if the difference ΔQ between the target amount of fuel injection (predetermined amount FQ) and the actual fuel injection amount RQ is equal to or greater than the determination value J, that is, when the error in the amount of injection is great and thereby the accuracy of fuel cetane number estimation is likely to decrease, the execution of estimation of the cetane number of the fuel supplied to the diesel engine 11 is limited. This allows the effect of estimation of the cetane number of the fuel at low accuracy to be suppressed and thus the cetane number of the fuel to be estimated accurately. In addition, even if the error in the amount of injection may be great, the cetane number of the fuel can be estimated on the condition that the time elapsed after the last execution of estimation of the fuel cetane number is long.

Other Embodiments

The above-described embodiments may be modified as follows.

In the first embodiment, if the difference $\Delta Q$ between the predetermined amount FQ and the actual fuel injection amount RQ is equal to or greater than the determination value J, the execution of estimation of the fuel cetane number is inhibited. The execution may be instead limited. Specifically, instead of estimating the fuel cetane number based only on the rotational fluctuation amount $\Sigma\Delta NE$ of the moment, a gradual change value of the rotational fluctuation amount $\Sigma\Delta NE$ may be calculated through, for example, a relational expression [previous value+(current value−previous value)×N, where (0<N<1)] and the like, and, based on the gradual change value, the fuel cetane number may be estimated. The degree of reflection to the gradual change value of the detected rotational fluctuation amount $\Sigma\Delta NE$ of the moment may then be reduced by, for example, resetting "N" in the relational expression to a smaller value if the difference $\Delta Q$ is equal to or greater than the determination value J.

In the processing of step S301 in the estimation control processing of the second embodiment, it may be determined whether or not the number of times in which the estimation of the fuel cetane number is inhibited (the number of YES determinations in the processing of step S206) is equal to or greater than a predetermined number of times. In addition, it may be determined whether or not the operation time of the diesel engine 11 after the last execution of estimation of the fuel cetane number is equal to or longer than a predetermined period of time and/or the travel distance of the vehicle 10 after the last execution of estimation of the fuel cetane number is equal to or greater than a predetermined value. It may further be determined whether or not the total amount of fuel injection (or intake amount) after the last execution of estimation of the fuel cetane number is equal to or greater than a predetermined amount.

In the second embodiment, the predetermined value P is corrected based on a value obtained by subtracting the predetermined amount FQ from the actual fuel injection amount RQ. The rotational fluctuation amount $\Sigma\Delta NE$ may be instead corrected based on the value. Such an arrangement allows the rotational fluctuation amount $\Sigma\Delta NE$ to be corrected according to the error in the rotational fluctuation amount $\Sigma\Delta NE$ due to an error in the amount of injection, when it may be great (see the outlined arrows in FIG. 6). Based on the rotational fluctuation amount $\Sigma\Delta NE$, it is therefore possible to accurately estimate whether the cetane number of the fuel supplied to the diesel engine 11 is within the lower cetane number region or the higher cetane number region.

In the estimation control processing of the respective embodiments, the processing (step S203) of correcting the target injection timing TQst and the target injection time TQtm using the correction terms K1 and K2 may be omitted as long as errors in the fuel injection timing and/or fuel injection amount due to, for example, initial individual variability and/or variation over time of the fuel injection valve 20 can be properly suppressed.

In the processing of step S206 in the estimation control processing of the respective embodiments, instead of determining whether or not the difference $\Delta Q$ between the actual fuel injection amount RQ and the predetermined amount FQ is equal to or greater than the determination value J, it may be determined whether or not the ratio between the actual fuel injection amount RQ and the predetermined amount FQ ([RQ/FQ] or [FQ/RQ]) is out of a predetermined range including 1.0. The point is that any condition may be employed for the determination in the processing of step S206 as long as being capable of determining that the difference between the actual fuel injection amount RQ and the predetermined amount FQ increases to the extent that there is a possibility of an excessive reduction in the accuracy of cetane number estimation.

The cetane number estimation devices of the respective embodiments may also be applied through appropriate modifications of the configurations to devices for determining, based on the rotational fluctuation amount $\Sigma\Delta NE$, to which one of three or more regions separated with respect to the fuel cetane number the actual fuel cetane number belongs.

The cetane number estimation device of the first embodiment may also be applied through appropriate modifications of the configuration not only to devices for determining, based on the rotational fluctuation amount $\Sigma\Delta NE$, to which of the lower cetane number region and the higher cetane number region the actual fuel cetane number belongs, but also to devices for estimating the fuel cetane number itself based on the rotational fluctuation amount $\Sigma\Delta NE$.

As engine control performed according to the fuel cetane number estimated through the estimation control processing, instead of or in addition to employing fuel injection control for the operation of the diesel engine 11, EGR control and/or pilot injection control may be performed, for example. The point is that any engine control may be employed to be performed according to the fuel cetane number as long as the state of fuel combustion is changed.

The processing of setting the target injection timing TQst based on the engine rotational speed NE (step S202) may be omitted as long as the invention is applied to devices in which the variation in the rotational fluctuation amount $\Sigma\Delta NE$ due to the difference in the engine rotational speed NE can be reduced to be small, such as devices in which the processing for estimation of the fuel cetane number is performed on the condition that the engine rotational speed NE lies within a limited narrow range.

A value other than the rotational fluctuation amount $\Sigma\Delta NE$ may be calculated as an index value of an output torque of the diesel engine 11. For example, the engine rotational speed NE when the fuel injection is performed and the engine rotational speed NE immediately before the fuel injection may be detected independently during the estimation control and the difference between the speeds may be calculated and used as the index value.

The mounting manner of the pressure sensor 41 may be modified into any manner without limiting the manner of directly mounting on the fuel injection valve 20 as long as the pressure serving as an index of the fuel pressure inside the fuel injection valve 20 (specifically, inside the nozzle chamber 25), that is, the pressure changing in connection with the change in the fuel pressure can be detected properly. Specifically, the pressure sensor may be mounted on the branch passage 31a or the common rail 34.

Instead of the fuel injection valve 20, which is of a type driven by the piezoelectric actuator 29, a fuel injection valve may be employed of a type driven by an electromagnetic actuator including, for example, a solenoid coil or the like.

The cetane number estimation devices of the embodiments may be employed not only to the vehicle 10 equipped with the clutch mechanism 13 and the manual transmission 14, but also to vehicles equipped with a torque converter and an automatic transmission. In these vehicles, the fuel injection for estimation of the fuel cetane number may be performed when the [condition 1] and [condition 3] are met, for example. In vehicles in which a torque converter incorporates a lock-up clutch, a new [condition 4] that the lock-up clutch should not be in an engaged state may be set and the fuel injection for estimation of the fuel cetane number may be performed on the condition that the [condition 4] is also met.

The present invention may also be applied to a diesel engine having one cylinder, a diesel engine having two cylinders, a diesel combustion engine having three cylinders and a diesel engine having five or more cylinders, in addition to the diesel engine having four cylinders.

DESCRIPTION OF THE REFERENCE NUMERALS

10 . . . vehicle, 11 . . . diesel engine, 12 . . . crankshaft, 13 . . . clutch mechanism, 14 . . . manual transmission, 15 . . . wheel, 16 . . . cylinder, 17 . . . intake passage, 18 . . . piston, 19 . . . exhaust passage, 20 . . . fuel injection valve, 21 . . . housing, 22 . . . needle valve, 23 . . . injection hole, 24 . . . spring, 25 . . . nozzle chamber, 26 . . . pressure chamber, 27 . . . introduction passage, 28 . . . communication passage, 29 . . . piezoelectric actuator, 29a . . . valve element, 30 . . . discharge passage, 31a . . . branch passage, 31b . . . supply passage, 32 . . . fuel tank, 33 . . . fuel pump, 34 . . . common rail, 35 . . . return passage, 40 . . . electronic control unit, 41 . . . pressure sensor, 42 . . . crank sensor, 43 . . . acceleration sensor, 44 . . . vehicle speed sensor, 45 . . . clutch switch.

The invention claimed is:

1. A cetane number estimation device, comprising:
    a fuel injection sensor configured to detect an actual amount of fuel injection, which is the actual amount of fuel injection through a fuel injection valve, through drive control of the fuel injection valve based on a target amount of fuel injection; and
    an electronic control unit, configured to:
        after determining that a fuel cutoff condition has been satisfied, perform a fuel injection for estimation of the cetane number of fuel supplied to a diesel engine through drive control of the fuel injection valve based on the target amount of fuel injection and detect an index value of an output torque of the diesel engine produced as a result of the fuel injection to estimate the cetane number of the fuel based on the detected index value; and
        calculate a difference between the target amount of fuel injection and the actual amount of fuel injection through the fuel injection valve through the drive control of the fuel injection valve,
        wherein, based on the target amount of fuel injection being equal to or greater than a determination value, prevent estimation of the cetane number, and based on the target amount of fuel injection being less than the determination value, perform estimation of the cetane number; and
        change an injection timing based on an engine rotational speed to reduce a variation in a rotational fluctuation amount due to a difference in the engine rotational speed.

2. The cetane number estimation device according to claim 1, wherein the fuel injection sensor is a pressure sensor for detecting a fuel pressure serving as an index of the fuel pressure inside the fuel injection valve, and the electronic control unit is configured to detect the actual amount of fuel injection based on the manner in which the fuel pressure detected by the pressure sensor fluctuates.

3. The cetane number estimation device according to claim 2, wherein the pressure sensor is mounted on the fuel injection valve.

4. The cetane number estimation device according to claim 1, wherein the electronic control unit is further configured to execute estimation of the cetane number on the condition that the fuel injection for operation of the diesel engine is stopped.

* * * * *